(12) United States Patent
Lattimore (10) Patent No.: US 10,076,598 B2
(45) Date of Patent: Sep. 18, 2018

(54) AUTOMATED PERITONEAL DIALYSIS SYSTEM USING A PERISTALTIC PUMP AND NON-CONTACT SENSORS

(71) Applicant: James Dean Lattimore, Fairport, NY (US)

(72) Inventor: James Dean Lattimore, Fairport, NY (US)

( * ) Notice: Subject to any disclaimer, the term of this patent is extended or adjusted under 35 U.S.C. 154(b) by 143 days.

(21) Appl. No.: 15/083,510

(22) Filed: Mar. 29, 2016

(65) Prior Publication Data

US 2016/0287773 A1    Oct. 6, 2016

Related U.S. Application Data

(60) Provisional application No. 62/121,662, filed on Apr. 4, 2015.

(51) Int. Cl.
*A61M 1/28* (2006.01)
*A61M 39/22* (2006.01)
*A61M 1/16* (2006.01)

(52) U.S. Cl.
CPC ............ *A61M 1/282* (2014.02); *A61M 1/166* (2014.02); *A61M 1/28* (2013.01); *A61M 39/22* (2013.01); *A61M 2205/3331* (2013.01); *A61M 2205/3334* (2013.01); *A61M 2205/3368* (2013.01); *A61M 2205/36* (2013.01); *A61M 2205/3653* (2013.01)

(58) Field of Classification Search
CPC ........ A61M 1/282; A61M 1/28; A61M 1/284; A61M 1/166; A61M 5/142; A61M 39/22; A61M 2205/3331; A61M 2205/3334; A61M 2205/3368; A61M 2205/36; A61M 2205/3653; A61M 39/20; A61M 39/12; A61M 39/1011; A61M 39/1033
See application file for complete search history.

(56) References Cited

U.S. PATENT DOCUMENTS

| | | | |
|---|---|---|---|
| 8,267,885 | B2 | 9/2012 | Landherr et al. |
| 8,641,659 | B2 | 2/2014 | Soykan et al. |
| 8,858,787 | B2 | 10/2014 | Muller et al. |
| 9,168,333 | B2 | 10/2015 | Kelly et al. |
| 9,216,246 | B2 | 12/2015 | Kelly et al. |
| 2003/0113931 | A1 | 6/2003 | Pan et al. |
| 2005/0131332 | A1* | 6/2005 | Kelly ................. A61M 1/1696 604/4.01 |

(Continued)

*Primary Examiner* — Imani Hayman
*Assistant Examiner* — Tezita Watts (57) ABSTRACT

An automated peritoneal dialysis therapy device includes pump tubing for delivering dialysate to a patient and for removing waste from the patient; a retractable peristaltic pump assembly; and a processor for controlling operations of the automated peritoneal dialysis therapy device. The retractable peristaltic pump assembly includes a retractable peristaltic pump having a pump rotor and a pump base, a heating source, located in the pump base, to heat the dialysate, a first temperature sensor to measure a temperature of the heating source, a second temperature sensor to measure a temperature of the dialysate, a flow sensor to measure an amount of dialysate being pumped, a pressure sensor to measure a pressure of the dialysate being pumped, and a motor to rotate the pump rotor. The processor controls rotational speed, displacement, and a direction of the pump rotor.

19 Claims, 5 Drawing Sheets

(56) References Cited

U.S. PATENT DOCUMENTS

| | | | |
|---|---|---|---|
| 2008/0015493 A1* | 1/2008 | Childers | A61M 1/1696 604/29 |
| 2009/0007642 A1* | 1/2009 | Busby | A61M 1/28 73/61.44 |
| 2009/0124963 A1* | 5/2009 | Hogard | A61M 1/16 604/30 |
| 2013/0220907 A1* | 8/2013 | Fulkerson | A61M 1/1692 210/186 |
| 2015/0005699 A1* | 1/2015 | Burbank | A61M 1/285 604/29 |
| 2015/0150715 A1* | 6/2015 | Svitek | A61M 1/369 422/46 |
| 2015/0374895 A1 | 12/2015 | Friederichs et al. | |
| 2016/0008529 A1 | 1/2016 | Hoffman | |

* cited by examiner

AUTOMATED PERITONEAL DIALYSIS SYSTEM USING A PERISTALTIC PUMP AND NON-CONTACT SENSORS

PRIORITY INFORMATION

This application claims priority from U.S. Provisional Patent Application, Ser. No. 62/121,662, filed on Apr. 4, 2015. The entire content of U.S. Provisional Patent Application, Ser. No. 62/121,662, filed on Apr. 4, 2015, is hereby incorporated by reference.

BACKGROUND

Kidneys of the human body function to remove excess fluids as well as some ions. The functional unit of the kidney is the nephron. A nephron consists of a filtering unit of tiny blood vessels called a glomerulus attached to a tubule. When blood enters the glomerulus, it is filtered and the remaining fluid then passes along the tubule. In the tubule, chemicals and water are either added to or removed from this filtered fluid according to the body's needs, and the final product is urine, which is excreted.

In patients with chronic kidney disease, kidney function is severely compromised. Chronic kidney disease, also known as chronic renal disease, is a progressive loss in renal function over a period of months or years. The most severe stage of chronic kidney disease is End Stage Renal Disease, which occurs when the kidneys cease to function.

The two main causes of chronic kidney disease are diabetes and high blood pressure, which are responsible for up to two-thirds of the cases. Heart disease is the leading cause of death for all people having chronic kidney disease. Excessive fluid can accumulate in patients suffering from end stage renal disease. The mortality rate of end stage renal disease patients who receive traditional hemodialysis therapy is 24% per year with an even higher mortality rate among diabetic patients.

Fluid accumulates in end stage renal disease patients because the kidneys can no longer effectively remove water and other fluids from the body. The fluid accumulates first in the blood and then accumulates throughout the body, resulting in swelling of the extremities and other tissues as edema. This accumulation of fluid causes increased stress on the heart, in turn causing significant increases in blood pressure or hypertension, which can lead to heart failure.

Although the population of patients afflicted with chronic kidney disease grows each year, there is no cure. Current treatments for chronic kidney disease seek to slow the progression of the disease. However, as the disease progresses, renal function decreases, and, eventually, renal replacement therapy is employed to compensate for lost kidney function. Renal replacement therapy entails either transplantation of a new kidney or dialysis.

Methods to treat kidney disease require the processing of blood to extract waste components such as urea and ions. The traditional treatment for kidney disease involves dialysis Dialysis emulates kidney function by removing waste components and excess fluid from a patient's blood. This is accomplished by allowing the body fluids, usually the blood, to come into the close proximity with the dialysate, which is a fluid that serves to cleanse the blood and actively remove the waste components and excess water. During this process, the blood and dialysate are separated by a dialysis membrane, which is permeable to water, small molecules (such as urea), and ions but not permeable to the cells. Each dialysis session lasts a few hours and may be repeated as often as three times a week.

Traditional processes, such as dialysis, require extracorporeal processing of body fluids. Once the blood is purified, it is then returned to the patient. Although effective at removing waste components from blood, dialysis treatments are administered intermittently and, therefore, do not emulate the continuous function of a natural kidney. Once the dialysis session is completed, the fluid begins to accumulate again in the tissues of the patient.

The benefits of dialysis notwithstanding, statistics indicate that three out of five dialysis patients die within five years of commencing treatment. Studies have shown that increasing the frequency and duration of dialysis sessions can improve the survivability of dialysis patients. Increasing the frequency and duration of dialysis sessions more closely resembles the continuous kidney function sought to be emulated. However, the extracorporeal processing of the body fluids increases the discomfort, inconvenience and the costs associated with treatment. There is also an additional risk of infection, which mandates that the procedures be carried out under the supervision of trained medical personnel.

Wearable dialysis units have been conceived in which the various components of the dialysis unit are miniaturized and made portable. The utility of these units remains limited due to the requirement that the blood must be brought outside of the body for filtering and due to the necessity for frequent servicing of the parts.

An alternative to a wearable dialysis system is an implantable dialysis device. With conventional implantable dialysis devices, most of the components are implanted, and the blood does not leave the patient's body. This type of unit suffers from difficulties related to the need for surgery to replace the internal parts, generally resulting from growth of tissue over the surfaces of the device that are exposed to tissue fluids, which results in reduced efficiency of the filtration.

Another clinical solution for kidney disease is peritoneal dialysis. In peritoneal dialysis, dialysate is infused into the peritoneal cavity. The peritoneal membrane serves as a natural dialyzer, and waste components diffuse from the patient's bloodstream across the peritoneal membrane into the dialysis solution via an osmotic gradient.

Under local anesthesia, a many-eyed catheter is sutured in place in the peritoneum and a sterile dressing is applied. The amount and the kind of dialysate and the length of time for each exchange cycle vary with the age, size, and condition of the patient.

There are three phases in each cycle. During inflow, the dialysate is introduced into the peritoneal cavity. During equilibration (swell), the dialysate remains in the peritoneal cavity. By means of osmosis, diffusion, and filtration, the needed electrolytes pass via the vascular peritoneum to the blood vessels of the abdominal cavity, and the waste products pass from the blood vessels through the vascular peritoneum into the dialysate.

During the third phase (drain), the dialysate is allowed to drain from the peritoneal cavity by gravity. The dialysis solution is removed, discarded, and replaced with fresh dialysis solution on a semi-continuous or continuous basis. Patients are able to replace the fluid periodically and care for the access ports.

This particular treatment causes discomfort due to excess amounts of fluid being pumped in and out of the abdominal area and retrograde flow into the bloodstream, which can increase fluid retention and the risk of infections. Further, medication for pain may be necessary.

Peritoneal dialysis may result in several complications, including perforation of the bowel, peritonitis, atelectasis, pneumonia, pulmonary edema, hyperglycemia, hypovolemia, hypervolemia, and adhesions.

Peritonitis, the most common problem, is usually caused by failure to use aseptic technique and is characterized by fever, cloudy dialysate, leukocytosis, and abdominal discomfort.

As noted above, in peritoneal dialysis, sterile peritoneal solution is infused into a patient's peritoneal cavity using a catheter that has been inserted through the abdominal wall. The solution remains in the peritoneal cavity for a dwell period. Osmosis exchange with the patient's blood occurs across the peritoneal membrane, removing urea and other toxins and excess water from the blood. Ions that need to be regulated are also exchanged across the membrane. The removal of excess water results in a higher volume of fluid being removed from the patient than is infused. The net excess is called ultrafiltrate, and the process of removal is called ultrafiltration. After the dwell time, the dialysate is removed from the body cavity through the catheter.

Peritoneal dialysis requires the maintenance of strict sterility because of the high risk of peritoneal infection. The risk of infection is particularly high due to the long periods of time that the patient is exposed to the dialysate.

In one form of peritoneal dialysis, which is sometimes referred to as cycler-assisted peritoneal dialysis, an automated cycler is used to infuse and drain dialysate. This form of treatment can be done automatically at night while the patient sleeps. One of the safety mechanisms for such a treatment is the monitoring by the cycler of the quantity of ultrafiltrate. The cycler performs this monitoring function by measuring the amount of fluid infused and the amount removed to compute the net fluid removal.

The treatment sequence usually begins with an initial drain cycle to empty the peritoneal cavity of spent dialysate, except on so-called "dry days" when the patient begins automated treatment without a peritoneum filled with dialysate. The cycler then performs a series of fill, dwell, and drain cycles, typically finishing with a fill cycle.

The fill cycle presents a risk of over-pressurizing the peritoneal cavity, which has a low tolerance for excess pressure.

In traditional peritoneal dialysis, a dialysate container is elevated to certain level above the patient's abdomen so that the fill pressure is determined by the height difference.

Automated systems sometimes employ pumps that cannot generate a pressure beyond a certain level, but this system is not foolproof since a fluid column height can arise due to a patient-cycler level difference and cause an overpressure.

A reverse height difference can also introduce an error in the fluid balance calculation because of incomplete draining.

Modern cyclers may fill by regulating fill volume during each cycle. The volume may be entered into a controller based on a prescription. The prescription, which also determines the composition of the dialysate, may be based upon the patient's size, weight, and other criteria.

Due to errors, prescriptions may be incorrect or imperfectly implemented resulting in a detriment to patient well-being and health.

Systems that measure pressure have been proposed. For example, a pressure sensor in contact with a fluid circuit at the cycler has been described. The sensor indicates the pressure at the proximal end of the fill/drain line. During operation, a controller connected to the pressure sensor changes the operation of the peritoneal dialysis machine in response to changes in pressure sensed by the pressure sensor.

Examples of peritoneal dialysis system are described in U.S. Pat. Nos. 8,267,885; 8,641,659; Published US Patent Application Number 2015/0005699; and Published US Patent Application Number 2016/0008529.

The entire contents of U.S. Pat. Nos. 8,267,885; 8,641,659; Published US Patent Application Number 2015/0005699; and Published US Patent Application Number 2016/0008529 are hereby incorporated by reference.

Peritoneal dialysis is a medical procedure for removing toxins from the blood that takes advantage of the semi-permeable membrane surrounding the walls of the abdomen or peritoneal cavity.

During a peritoneal dialysis procedure, a solution is introduced into the patient's abdomen, where it remains for up to several hours, removing blood toxins via osmotic transfer through the peritoneal membrane. At completion of the procedure, the solution is drained from the body along with the toxins. In automated peritoneal dialysis, the entire procedure is handled by automated equipment; often times in the patient's home while they sleep.

There are many systems for performing automated peritoneal dialysis. Typically, such systems include complex pumping means and a variety of other complex components including noisy pumps and valves to insure accurate delivery of fluid volume and temperature.

In today's economy with the high cost of healthcare, cost is an ever-increasing issue, and many automated peritoneal dialysis equipment manufacturers have attempted to reduce production costs by several means. One is to employ peristaltic pumps, which can be inexpensive, though have inherent limitations.

For example, accurately measuring the fluid volume when delivered by a peristaltic pump can be difficult because the tubing used in the pump is elastic. So consequently, the tubes volume may change over time as well as the pump displacement or rotations must be closely tracked to monitor fluid flow accurately.

Peristaltic pumps also have a tendency to develop pinhole leaks in pump tubing after extended use and can trap fluids between uses which could result in its loss of sterility following repeated uses.

The pump tube is usually a fixed component of the pump and thus is subject to failure due to wear or fracture and can also be difficult to insure its sterility between uses.

Therefore, it is desirable to provide an automated peritoneal dialysis therapy device that delivers temperature controlled volumes of fluids to a patient accurately using a peristaltic pump with both indirect and direct methods of measurement for redundancy.

It is further desirable to provide an automated peritoneal dialysis therapy device that delivers temperature controlled volumes of fluids to a patient accurately using a peristaltic pump by providing a direct determination of fluid volume, flow rate, and temperature using a non-contact solid-state sensor technology.

In addition, it is desirable to provide an automated peritoneal dialysis therapy device that delivers temperature controlled volumes of fluids to a patient accurately using a peristaltic pump by calculating a volume expected to be delivered by tracking effective displacement using a precisely indexed pump motor during actuation and a temperature sensor mounted in close proximity to the tube embedded into the pump base.

Also, it is desirable to provide an automated peritoneal dialysis therapy device that includes a retractable peristaltic pump roller mechanism, which includes cam driven multiple spring loaded pump rollers to allow the patient to easily retract the rollers and insert a disposable peristaltic pump tube into the pump base.

It is desirable to provide an automated peritoneal dialysis therapy device that can facilitate using a peristaltic pump where the pump tube is part of a single use disposable tubing set which can easily be assembled into a retracted pump mechanism by the user during setup, thereby eliminating the need for complex and costly cartridge assemblies and significantly reducing the possibility of system leaks or introduction of non-sterile matter into the patient line.

It is also desirable to provide an automated peritoneal dialysis therapy device that can facilitate using an in-line heating method where the fluid is heated inside the tube section passing through a peristaltic pump, and fluids are heated "on the fly" or simultaneously during the pumping process using heating elements and sensors embedded in the pump housing under a closed loop control process, thereby eliminating the need for heater methods and containers which require large percentages of entire therapy fluid volume (as much as 20 liters) be moved and placed on a bulk heater apparatus by the patient or caregiver and the entire volume heated to the proper temperature before the patients dialysate delivery or therapy can begin.

It is further desirable to provide an automated peritoneal dialysis therapy device that utilizes induction heating of the pump base and rotor and ultimately by conduction and radiation of the tube and the fluid inside.

Moreover, it is desirable to provide an automated peritoneal dialysis therapy device that can facilitate safe and efficacious automated peritoneal dialysis therapy in the privacy of the patient's home or other location where a reliable power source may be available.

BRIEF DESCRIPTION OF THE DRAWINGS

The drawings are only for purposes of illustrating various embodiments and are not to be construed as limiting, wherein.

DETAILED DESCRIPTION

For a general understanding, reference is made to the drawings. In the drawings, like references have been used throughout to designate identical or equivalent elements. It is also noted that the drawings may not have been drawn to scale and that certain regions may have been purposely drawn disproportionately so that the features and concepts could be properly illustrated.

Figure 1:
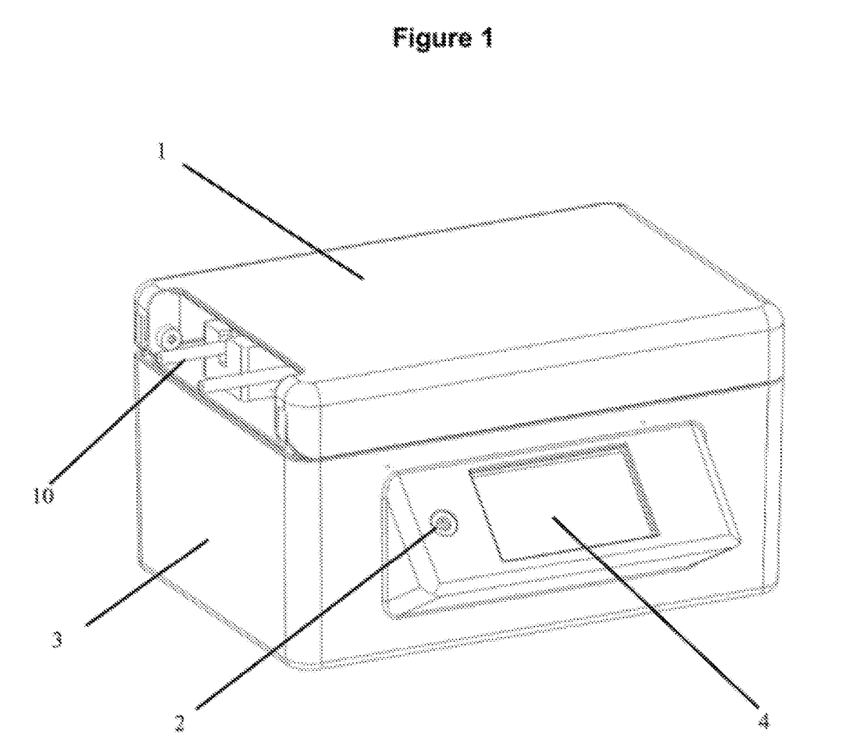
FIG. 1 is a perspective view of an automated peritoneal dialysis therapy device.

FIG. 1 illustrates an automated peritoneal dialysis therapy device, which includes a clear plastic top cover 1 in a closed position, a plastic main enclosure 3, an ON/OFF switch 2, a graphical user interface 4, a processor (not shown), and an exit for a disposable tube set 10.

The graphical user interface 4 may display information to assist a user in setting up the automated peritoneal dialysis therapy device; may display the system status of the automated peritoneal dialysis therapy device; may display the therapy status of the automated peritoneal dialysis therapy device; prescription information; and/or volumetric information, etc. This information may also be transmitted to a remote authorized user.

The graphical user interface 4 may also enable the user to set up the automated peritoneal dialysis therapy device; change or modify the system status of the automated peritoneal dialysis therapy device; and/or change or modify the therapy status of the automated peritoneal dialysis therapy device.

Figure 2:
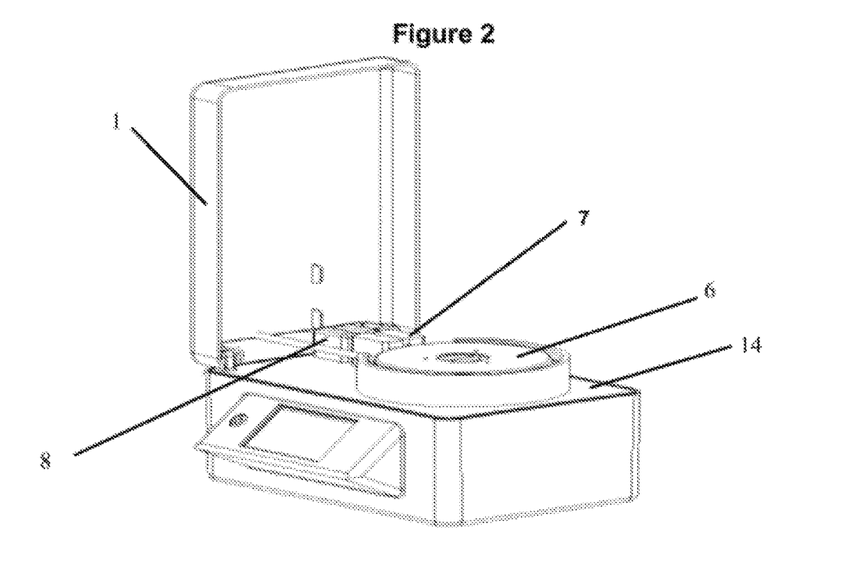
FIG. 2 is a perspective view of the automated peritoneal dialysis therapy device with its cover opening showing the disposable tube set and its path through the pump and sensors.

FIG. 2 illustrates the top cover 1 in an opened position. As illustrated in FIG. 2, a pump subsystem is located on a top mounting plate 14. The pump subsystem includes a retractable peristaltic pump assembly 6, a non-contact flow & temperature sensor 7, and a force sensor 8. The pump subsystem causes fluids to flow through the disposable tube set 10.

An aesthetic cover (not shown) may be attached to the top mounting plate 14 for covering of the sensors and pump assembly. The aesthetic cover would include a slot to help guide the user in proper placement of the pump section of the disposable tube set 10. The aesthetic cover enables easier cleaning and a prominent surface for the presentation of labels and/or setup instructions to the user.

The retractable peristaltic pump assembly 6 is composed of stainless steel parts and roller bearings.

Figure 3:
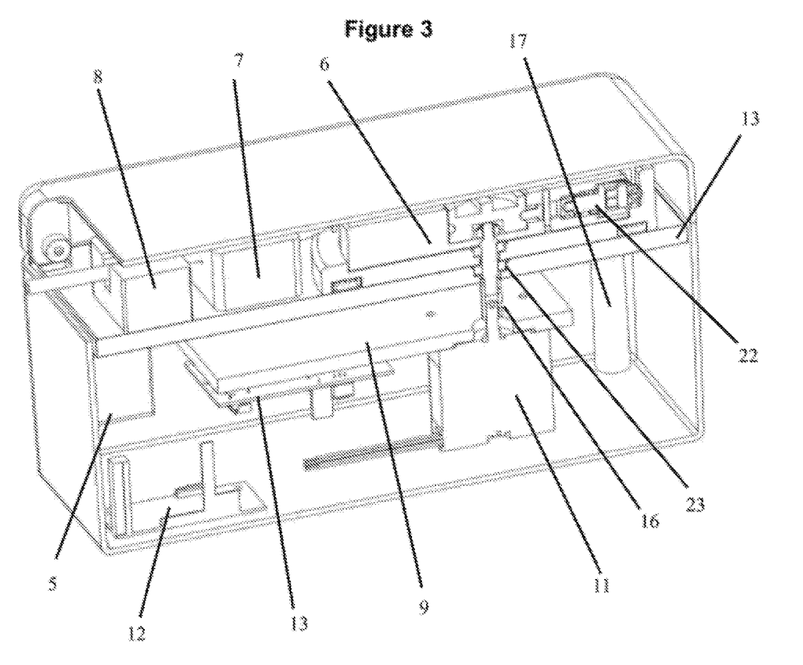
FIG. 3 is a lengthwise cross-section view of the system showing internal components of the automated peritoneal dialysis therapy device.

As illustrated in FIG. 3, the disposable tube set 10 patient connection line passes through the non-contact flow & temperature sensor 7 and the force sensor 8. The non-contact flow & temperature sensor 7 can provide direct measurements of the fluid volume and fluid temperature.

The force sensor 8 measures expansion and contraction of the patient line tube diameter to determine pressure changes in the tube relative to atmospheric pressure, thereby determining the differential pressure in the patient's abdomen.

Further, as shown in FIG. 3, a pump drive mounting plate 9 provides mounting features for positioning a drive motor 11. The drive motor 11 is coupled to pump drive spindle 15 (FIG. 4) by shaft coupler 16.

The drive motor 11 is powered and/or indexed by drive motor drive circuitry 13 to advance pump rotor 20 (FIG. 4) of the retractable peristaltic pump assembly 6.

The pump drive mounting plate 9 is held to the bottom of the top mounting plate 14 using threaded spacers (not shown) and machine screws (not shown) with matching threads.

The automated peritoneal dialysis therapy device includes an AC/DC power supply 12 which can operate with a wide range of AC voltage sources, as found in use around the world. The AC/DC power supply 12 is connected to an external AC mains power source using a common modular 3-wire power cord which plugs into power entry module 5 which is wired to the AC/DC power supply 12 input terminals.

The power entry module 5 may also include fusing and line RF filtering needed to meet global electrical safety and EMC regulatory requirements. The AC/DC power supply 12 provides power to all control electronics and inductive power pulse generator 17 via a wiring harness (Not shown).

The inductive power pulse generator 17 supplies oscillating current to inductive heater coil 18 (FIG. 4), controlled by a processor (not shown).

The inductive heater coil 18 (FIG. 4) provides rapid and efficient heating of the pump base 19 (FIG. 4) and pump rotor 20 (FIG. 4), which in turns heats the fluid in the pump section of the disposable tube set 10, while the pump is running, through thermal conduction and radiation.

An embedded thermistor 27 (FIG. 4) provides temperature signals that enables closed loop control by the processor (not shown).

The drive motor 11 includes an integral encoder that provides signals indicative of the pump's direction, displacement, and speed, thereby enabling closed loop control of the pump as the integral encoder indexes the pump rotor. The integral encoder also facilitates the calculation of the expected displaced fluid volume produced by the pump.

All the automated peritoneal dialysis therapy device's functions are under the control of and are being monitored by control software programmed within the processor (not shown).

The heating of the dialysis solution while the fluid is being pumped dramatically reduces the time needed to ready the dialysis solution to deliver therapy than using a heater to heat large volumes of solution in a bag or other container.

It is noted that the inductive heater coil 18 (FIG. 4) operates when fluid is being delivered 'to' the patient, thus, the dialysis solution is heated to a tightly controlled temperature.

Figure 4:
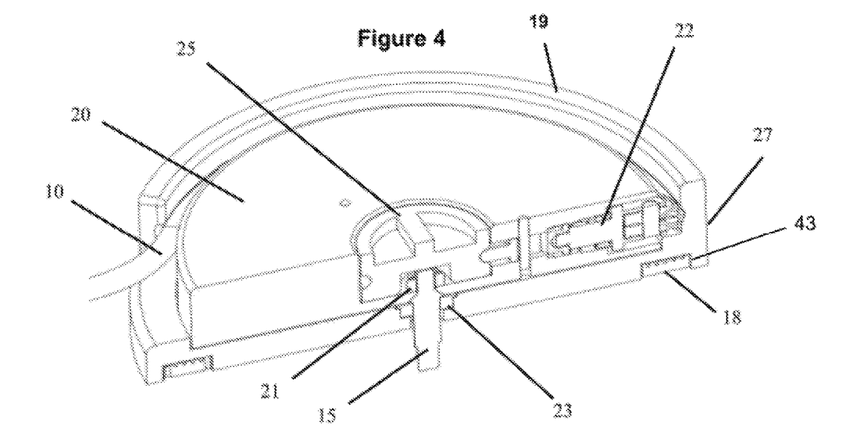
FIG. 4 is a lengthwise cross-section view of the peristaltic pump and heater assembly showing the internal parts and their relationships in the retracted position of the automated peritoneal dialysis therapy device.

As illustrated in FIG. 4, the pump rotor 20 houses multiple pump roller assemblies 22. For example, FIG. 5 illustrates three (3) pump roller assemblies 22.

Figure 5:
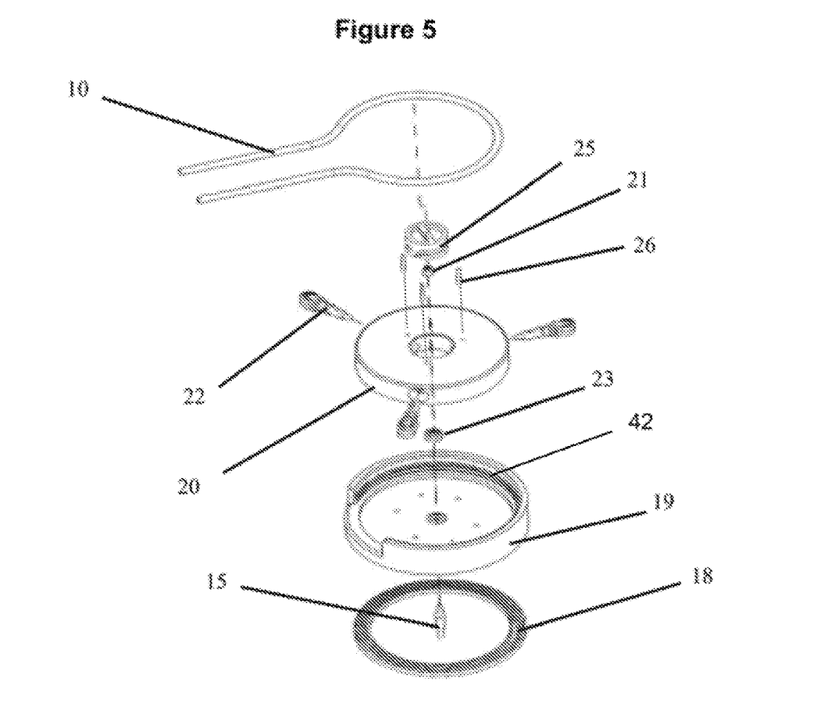
FIG. 5 is a lengthwise cross-section view of the peristaltic pump sub-assembly of the automated peritoneal dialysis therapy device showing the pump rollers in the engaged position and ready for pumping.

Each pump roller assemblies 22 is held in proper position inside the pump rotor 20 by a threaded retention ring 28 (FIG. 6) and dowel pins 26 (FIG. 5).

The pump roller assemblies 22 are held toward the center of the retractable peristaltic pump assembly 6 and against pump engagement cam knob 25 by preloading a compression spring 29 (FIG. 6) within the pump rotor 20 using the threaded retention ring 28 (FIG. 6), while being oriented and having its travel limited by the dowel pins 26 (FIG. 5).

This implementation provides the engagement and retraction of the pump roller assemblies 22 via rotation of the pump engagement cam knob 25 by the user. The displacement of the pump roller assemblies 22 is proportional to the axial displacement of the pump engagement cam knob 25 cam surface relative to its axis of rotation.

Figure 6:
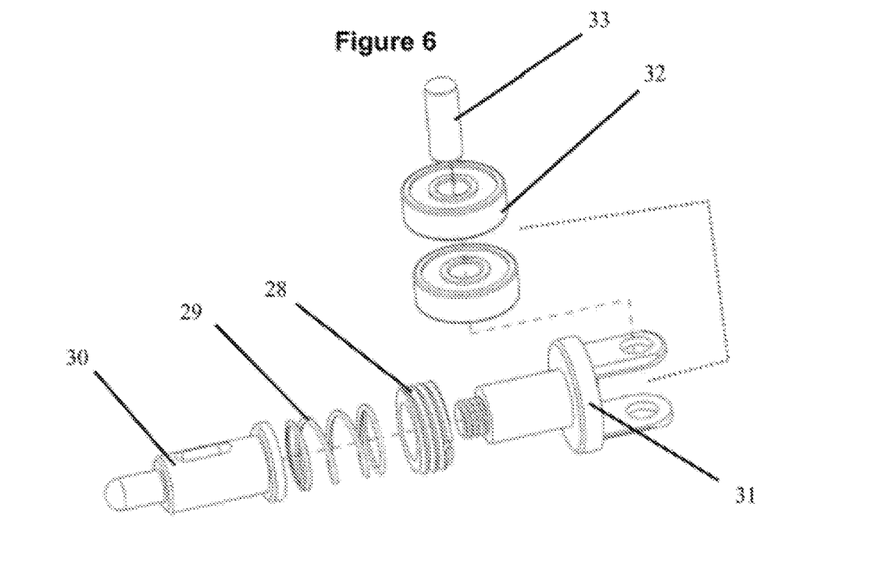
FIG. 6 is an exploded view of the pump roller sub-assembly of the automated peritoneal dialysis therapy device.
Figure 7:
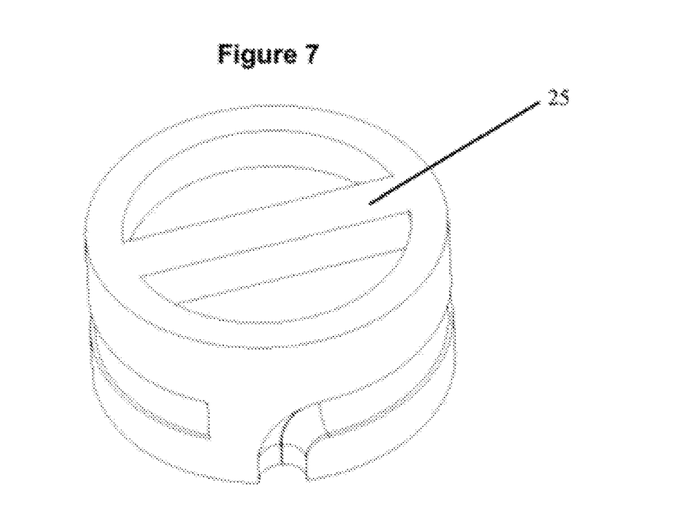
FIG. 7 is a perspective view of the pump engagement cam knob of the automated peritoneal dialysis therapy device.

The pump engagement cam knob 25 is held in place by the cam follower tip of the inner cam follower 30 (FIG. 6) resting in a detent or over travel position of the pump engagement cam knob 25 (FIG. 7).

The pump roller assemblies 22, for example, may move in or out of the pump rotor 20 perpendicular to the retractable peristaltic pump assembly 6 axis of rotation by 6 mm with an approximate 105 degree turn of the pump engagement cam knob 25 by the user.

Following the user's inserting the pump tube section of the disposable tube set 10 into the tube locating groove 42 of pump base 19 (FIG. 5) and through non-contact flow & temperature sensor 7 and the force sensor 8, the pump is prepared for moving fluid by the user rotating the pump engagement cam knob 25 to its engaged and locked position.

This pump implementation method allows the user to quickly and easily insert a very inexpensive, fresh, and sterile disposable tube set 10 into the peristaltic pump apparatus in preparation for pumping, thereby eliminating the need for expensive complex cassette assemblies or the requirement to flush and/or sterilize permanent tubes used by conventional peristaltic pumps between uses.

Further as shown in FIG. 4, spindle bearing 23 rests atop the pump drive spindle 15 mounted in the center of the pump base 19 and supports the pump rotor 20 and attached pump roller assemblies 22 via a mating conical surface on top of the pump drive spindle 23 and the bottom of the pump rotor 20.

This insures the pump rotor 20 is supported parallel to the pump base 19 and maintains adequate clearance relative to the pump base 19 while being held securely by the lock nut 21.

The pump drive spindle 23 is inserted into the spindle bearing 23 located in the top mounting plate 14, which further stabilizes the pump drive spindle 15.

The pump drive spindle 23 bears the reaction forces generated by the disposable tube set 10 being compressed by the pump roller assemblies 22 when the pump engagement cam knob 25 is in the engaged position and the pump rotor 20 is being rotated by the drive motor 11 via the shaft coupler 16.

A thermally insulative hard plastic material is used for the top mounting plate 14 to concentrate heat generation in the pump base 19 and the pump rotor 20. The thermally insulative hard plastic material also helps isolate the heat source from the remainder of the system.

The retractable peristaltic pump assembly 6, the non-contact flow & temperature sensor 7, and the force sensor 8 are held in their appropriate positions along the path of the patient connection end of the disposable tube set 10 by machine screws (not shown) entering from the opposite side of the top mounting plate 14.

As illustrated in FIG. 4, the pump base 19 holds the inductive or resistive heater coil 18 in a recess 43, located just below the path of the disposable tube set 10 within the retractable peristaltic pump assembly 6.

This location enables efficient and effective heat generation induced by the inductive heater coil 18 in the pump base 19 and pump rotor 20. The heat is induced by oscillating electrical currents supplied by the inductive power pulse generator 17.

The inductive heater coil 18 insures that the heat source is concentrated as close as possible to the fluid being heated and pumped, thereby providing for minimal resistance to heat transfer and providing faster fluid heating with better efficiency.

The thermistor 27 is mounted in the pump base 19, as close as possible to the tube groove 42, as shown in FIG. 4, so as to provide a direct measurement of inductive heater coil's temperature for closed loop control of the inductive heater coil 18 by the processor.

The pump base 19 and inductive heater coil 18 is connected as close as possible to the inductive power pulse generator 17 as shown in FIG. 3. The inductive power pulse generator 17 is connected with heavy gauge wire to the inductive heater coil 18 to minimize stray inductance and conductor power losses.

The thermistor 27 may be held in position using thermally conductive adhesive or epoxy. The inductive heater coil 18 may be held into position using pressure sensitive adhesive and/or machine screws.

The inductive heater coil 18 may be made by embedding a low resistance conductor, suitable for the current drawn by the heater, in a spiral pattern and in a plane inside a temperature resistant electrically insulative material.

As illustrated in FIG. 6, the compression spring 29 of the pump roller assemblies 22 facilitates the retraction of the peristaltic pump rollers so that the user can easily insert the pump tubing integral to the disposable tube set 10 and complete the retractable peristaltic pump assembly 6 in preparation for fluid transfer through the device.

Further, as illustrated in FIG. 6, inner cam follower 30 is inserted into each of the pump rotor 20 perimeter holes (not shown) small tip first and held in place by pressing the cam follower dowel pin 26 into a pump rotor 20 dowel hole and through a slot in the inner cam follower 30 body until the dowel is flush with the top surface of the pump rotor 20, thereby limiting the travel and rotation of pump roller assemblies 22 in the retractable peristaltic pump assembly 6.

Each inner cam follower 30 is preloaded with a compression spring 29 and held in place by a threaded spring retainer ring 28 screwed into the threads inside each hole of the pump rotor 20. The pump roller assemblies 22 are assembled by pressing the bearing dowel pin 33 into the roller mount 31, through the pump roller bearings 32 located between the two forks and back into the opposite fork of the roller mount 31 until flush with the surface.

Once assembled, each pump roller assembly 22 may include the addition of a small patch of common thread locking compound applied to the threads of the roller mount 31 prior to being inserted into the hole through the threaded spring retainer ring 28 and the compression spring 29 and then threaded into its mating threaded hole of the inner cam follower 30 until it bottoms out. Once the thread locking compound cures, it will hold the pump roller assembly 22 securely in the proper orientation and position for proper compression of the tubing needed for fluid movement.

The axis of the bearing dowel pin 33 and pump roller bearings 32 are aligned perpendicular to the top surface of the pump rotor 20 by backing out the roller mount 31 until perpendicularity is achieved The above described alignment minimizes rolling resistance and tube wear when the retractable peristaltic pump assembly 6 is in the engaged position and the pump rotor 20 is rotating under power provided by the drive motor 11. The pumping of fluid into or out of the patient is determined by the direction of rotation of the pump rotor 20.

Figure 8:
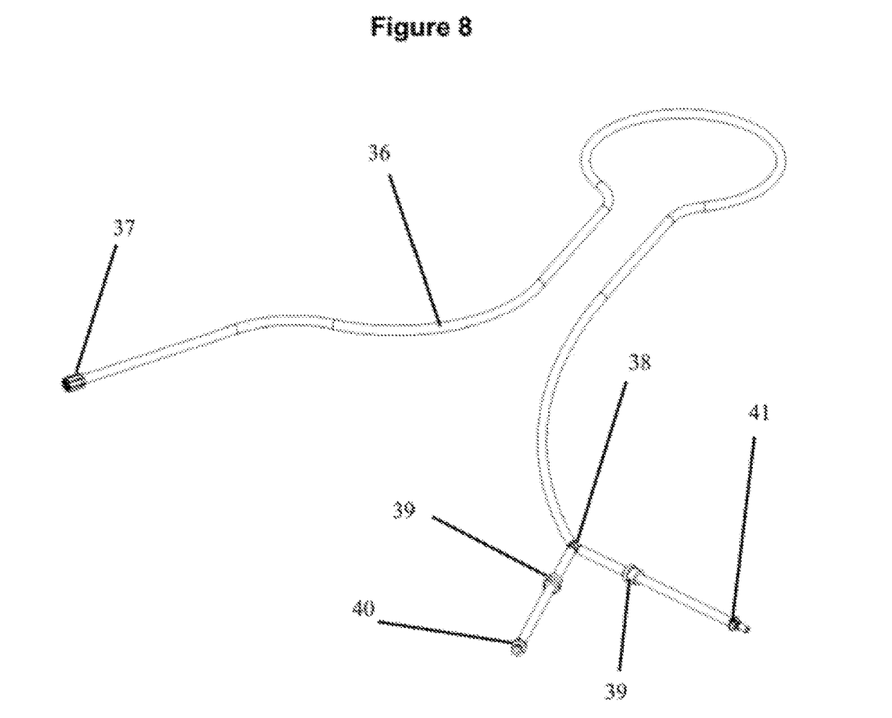
FIG. 8 is a perspective view of the disposable tube set of the automated peritoneal dialysis therapy device.

FIG. 8 illustrates the disposable tube set 10. The disposable tube set 10 is designed as a single use component or single use sub-assembly of the automated peritoneal dialysis therapy device. The disposable tube set 10 minimizes cost, while insuring safe and effective delivery of the prescribed therapy delivered by the system. For example, the disposable tube set 10 may be composed of low durameter flexible medical grade Flexible Tubing 36.

A suitable patient catheter connector 37 is attached on the patient connection end of a suitable length of tubing (6 to 10 feet), while a Y-connector 38 is attached on the opposite end of the disposable tube set 10. The 38 allows for separate connections to the dialysate source and waste lines In each of the two lines coupled to the Y-connector 38 a one-way valve 39 is included to insure that fluid being supplied to the patient is only allowed to flow from the source and fluids being extracted from the patient are only allowed to flow to the waste line for disposal.

Each of these lines includes distinct connectors, one for the supply connector 41 and another for the waste connector 40, thereby eliminating incorrect connections and/or contamination by the user.

Figure 9:
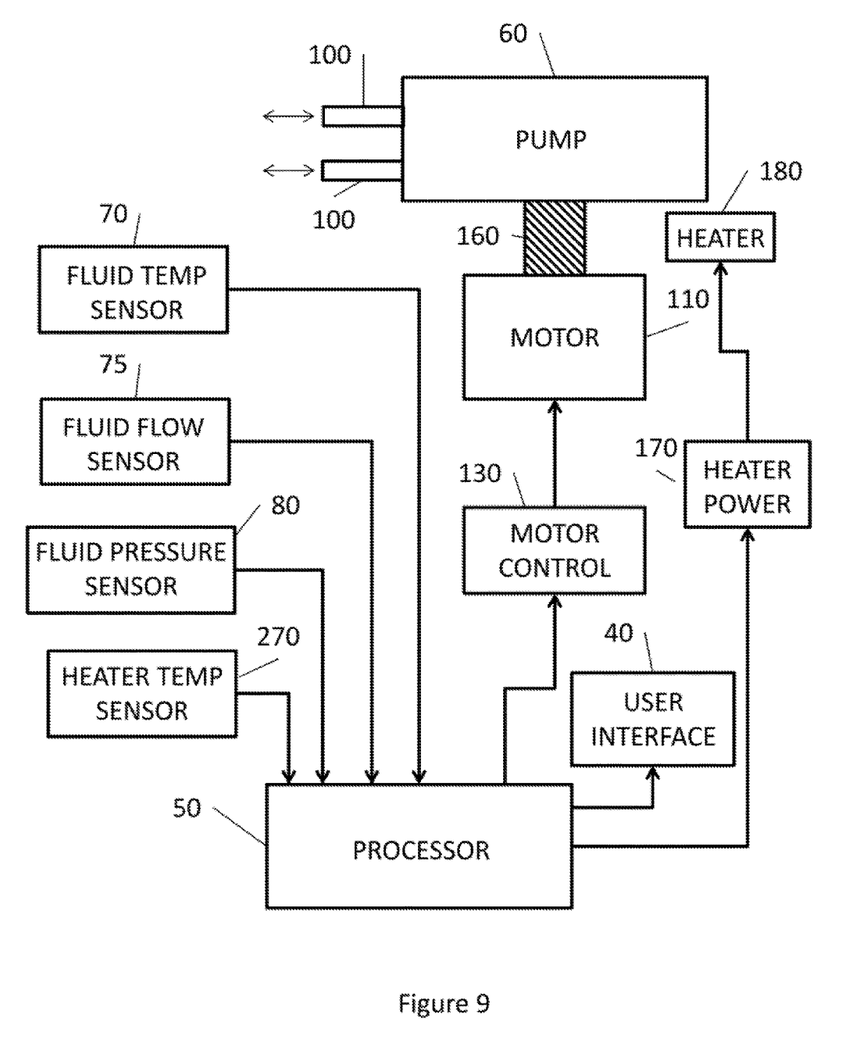
FIG. 9 is a block diagram of the automated peritoneal dialysis therapy device.

As illustrated in FIG. 9, the automated peritoneal dialysis therapy device includes a processor 50 operatively connected to non-contact fluid flow sensor 75, fluid temperature sensor 70, fluid pressure sensor 80, and heater temperature sensor 270.

The processor 50 is also operatively connected to a user interface 40, a motor control circuitry 130, and a heater power source 170. If the user interface 40 does not include a display, the processor 50 may also be operatively connected to a display device.

It is noted that the processor 50 may be connected to a communication device (not shown) which allows the automated peritoneal dialysis therapy device to communicate therapy data with medical personnel or the manufacturer to upload possible system software updates remotely.

The processor 50 provides control signals to the motor control circuitry 130. The motor control circuitry 130, in response to the control signals received from the processor 50, controls the rotational speed and rotational direction of the motor 110. The motor 110, via shaft 160, drives the rotational speed and rotational direction of the pump 60, which controls the flow and flow direction of the fluid in the tubing 10.

The processor 50 provides control signals to the heater power source 170. The heater power source 170, in response to the control signals received from the processor 50, controls the amount of heat generated by the heater 180.

With respect to the operations of the automated peritoneal dialysis therapy device, upon initiation of a dialysis procedure, the processor 50 provides control signals to the motor control circuitry 130 so that the motor control circuitry 130 and the motor 110 cause the pump 60 to begin to draw fluid (dialysate) from a source and pump the fluid (dialysate) into a patient.

During this dialysate providing procedure, the processor 50 provides control signals to the heater power source 170 so that the heater 180 can initiate operations to heat the dialysate to an appropriate temperature.

The processor 50 monitors both the fluid (dialysate) temperature, provided by fluid temperature sensor 70, and the temperature of the heater 180, provided by heater temperature sensor (thermistor) 270.

Based upon the information provided by the fluid temperature sensor 70 and the heater temperature sensor (thermistor) 270, the processor 50 will cause the heater power source 170 to increase or decrease to power being supplied to the heater 180, thereby regulating the temperature of the dialysate to an appropriate temperature.

The processor 50 monitors the pressure of the fluid (dialysate) being pumped into the patient via the fluid pressure sensor 80.

Based upon the information provided by the fluid pressure sensor 80, the processor 50 will cause, via the motor control circuitry 130 and the motor 110, the pump 60 to increase or decrease the rotational speed of the pump 60, thereby regulating the pressure of the dialysate.

The processor 50 monitors the amount of the fluid (dialysate) being pumped into the patient via the fluid flow sensor 75.

Based upon the information provided by the fluid flow sensor 75, the processor 50 will cause, via the motor control circuitry 130 and the motor 110, the pump 60 to stop pumping when a predetermined volume of the dialysate has been received by the patient.

It is noted that the processor 50 may control the speed of the pump based on the efficiency of the heater 180.

For example, if the temperature of the dialysate is too low and the heater 180 cannot maintain a higher temperature, the processor 50 will cause, via the motor control circuitry 130 and the motor 110, the pump 60 to decrease the rotational speed of the pump 60, thereby allowing the dialysate to engage the heater 180 for a longer period of time, as needed, to reach the targeted temperature.

On the other hand, for example, if the temperature of the dialysate is too high and the heater 180 cannot maintain a lower temperature, the processor 50 will cause, via the motor control circuitry 130 and the motor 110, the pump 60 to increase the rotational speed of the pump 60, thereby allowing the dialysate to engage the heater 180 for a lesser period of time, therefore reducing the heating of the fluid.

After the patient has received the appropriate amount of fluid (dialysate), the processor 50, after a predetermined period of time (dwell), will initiate the waste removal process. During the waste removal processor, the processor 50 will cause, via the motor control circuitry 130 and the motor 110, the pump 60 to reverse the rotational direction of the pump 60, thereby drawing waste product out of the patient and pumping the waste product to an appropriate waste disposal sub-system, such as a disposable waste container or nearby toilet.

The automated peritoneal dialysis therapy device, as described above, smaller and less expensive to operate as compared to conventional systems.

Moreover, the automated peritoneal dialysis therapy device, as described above, makes it easier for patients to travel with a peritoneal dialysis therapy device and to afford its use for their therapy. The automated peritoneal dialysis therapy device, as described above, also significantly reduces the user's or caregiver's need to lift large volumes of fluids and the relative time needed to heat the fluid in preparation to begin the therapy.

The automated peritoneal dialysis therapy device, as described above, minimizes the number of moving parts to reduce noise and improve system reliability.

The automated peritoneal dialysis therapy device, as described above, is computer controlled, using closed loop feedback and non-contact solid-state sensors in real time during system operation, thereby enabling confirmation of the fluid's characteristics before delivery to the patient.

Further, the disposable components of the automated peritoneal dialysis therapy device, reduces medical waste to be disposed of and the total cost of delivery of each therapy.

The above described automated peritoneal dialysis device or system utilizes a retractable mechanism to allow easy insertion of a section of the disposable patient tube set to complete the peristaltic pump mechanism; realizes simplified fluid volume and temperature tracking by utilizing a non-contact flow and temperature sensor; and utilizes a processor controlled pump motor and closed loop control system for key parameter control and tracking.

The above described automated peritoneal dialysis device or system also utilizes a heater integral to the pump housing that heats the solution being delivered to the patient while pumping and provides a cassette-free low cost disposable tube set for each delivered therapy.

The above described automated peritoneal dialysis device or system includes a user interface through a touchscreen graphical user interface which provides user controls, system status, and therapy status.

The processor and software can store patient therapy settings, therapy logs, and systems error logs, which can be changed or accessed via common solid state storage media and/or using various communication protocols or devices.

In summary, an automated peritoneal dialysis therapy device, includes tubing for delivering fluid to a patient and for removing waste from the patient; a pump assembly, operatively connected to the tubing, for causing the fluid to be delivered to the patient and for causing the waste to be removed from the patient; and a heating source, located in the pump assembly, to heat the fluid, as the fluid is being pumped, to a predetermined temperature.

The heating source may be an inductive or resistive heater coil.

The tubing may be disposable.

The pump assembly may include a retractable peristaltic pump.

The tubing may include a first connection for connecting to a patient, a second connection for connecting to a dialysate source, and a third connection for connecting to a waste removal system.

The fluid may be dialysate.

The automated peritoneal dialysis therapy device may include a non-contact flow and temperature sensor for measuring a flow and temperature of the fluid.

The pump assembly may include a groove to hold the pump tubing, and the heating source is located below the groove.

An automated peritoneal dialysis therapy device, includes tubing for delivering fluid to a patient and for removing waste from the patient; a retractable peristaltic pump assembly, operatively connected to the tubing, for causing the fluid to be delivered to the patient and for causing the waste to be removed from the patient; and a processor for controlling operations of the automated peritoneal dialysis therapy device.

The retractable peristaltic pump assembly includes, a retractable peristaltic pump having a pump rotor and a pump base, a heating source, located in the pump base, to heat the fluid, as the fluid is being pumped, to a predetermined temperature, a first temperature sensor to measure a temperature of the heating source, a second temperature sensor to measure a temperature of the fluid as the fluid leaves the retractable peristaltic pump, a flow sensor to measure an amount of fluid being pumped by the retractable peristaltic pump, a pressure sensor to measure a pressure of the fluid being pumped by the retractable peristaltic pump, and a motor to rotate the pump rotor to pump the fluid to the patient and to rotate the pump to draw waste from the patient and pump the waste to a waste removal system.

The processor is operatively connected to the first temperature sensor, the second temperature sensor, the flow sensor, the pressure sensor, the heating source, and the motor. The processor controls a rotational speed and a direction of the motor.

The heating source may be an inductive heater coil.

The heating source may include an inductive heater coil and an inductive power pulse generator to provide power to the inductive heater coil.

The tubing may be disposable.

The tubing may include a first connection for connecting to a patient, a second connection for connecting to a dialysate source, and a third connection for connecting to a waste removal system.

The fluid may be dialysate.

The processor may control the rotational speed of the motor based upon the measured pressure of the fluid being pumped by the retractable peristaltic pump.

The processor may control the rotational speed of the motor based upon the measured temperature of the heating source and the measured temperature of the fluid as the fluid leaves the retractable peristaltic pump.

The processor may control the rotational speed of the motor based upon the measured amount of fluid being pumped by the retractable peristaltic pump.

The processor may control the rotational direction of the motor to rotate in a first direction when fluid is being pumped into a patient by the retractable peristaltic pump and to rotate in a second direction when waste is being removed from the patient by the retractable peristaltic pump, the first direction being opposite the second direction.

An automated peritoneal dialysis therapy device, includes pump tubing for delivering fluid to a patient and for removing waste from the patient; a pump assembly, operatively connected to the pump tubing, for causing the fluid to be delivered to the patient and for causing the waste to be removed from the patient; and a heating source, located in the pump assembly, to heat the fluid, as the fluid is being pumped, to a predetermined temperature.

The heating source may be an inductive heater coil. The heating source may include an inductive power pulse generator to provide power to the inductive heater coil. The heating source may be a resistive heater coil.

The pump tubing may be disposable.

The pump tubing may include a first connection for connecting to a patient, a second connection for connecting to a fluid source, and a third connection for connecting to a waste removal system.

The second connection may include a one-way fluid valve, and the third connection may include a one-way fluid valve.

The fluid may be dialysate.

The automated peritoneal dialysis therapy device may include a non-contact flow and temperature sensor for measuring a flow and temperature of the fluid.

The pump assembly may include a groove to hold the pump tubing, and the heating source is located below the groove to transfer heat to the fluid while the pump assembly pumps the fluid.

The heating source may be integral to the pump assembly.

The pump assembly may be a retractable peristaltic pump assembly, operatively connected to the tubing, for causing the fluid to be delivered to the patient and for causing the waste to be removed from the patient, and the automated peritoneal dialysis therapy device may further include a processor for controlling operations of the automated peritoneal dialysis therapy device.

The retractable peristaltic pump assembly includes a retractable peristaltic pump having a pump rotor and a pump base, a heating source, located in the pump base, to heat the fluid, as the fluid is being pumped, to a predetermined temperature, a first temperature sensor to measure a temperature of the heating source, a second temperature sensor to measure a temperature of the fluid as the fluid leaves the retractable peristaltic pump, a flow sensor to measure an amount of fluid being pumped by the retractable peristaltic pump, a pressure sensor to measure a pressure of the fluid being pumped by the retractable peristaltic pump, and a motor assembly to rotate the pump rotor to pump the fluid to the patient and to rotate the pump to draw waste from the patient and pump the waste to a waste removal system.

The processor is operatively connected to the first temperature sensor, the second temperature sensor, the flow sensor, the pressure sensor, the heating source, and the motor assembly. The processor controls a rotational speed, a displacement, and a direction of the pump rotor.

The processor may control the rotational speed of the pump rotor based upon the measured pressure of the fluid being pumped by the retractable peristaltic pump.

The processor may control the rotational speed of the pump rotor based upon the measured temperature of the heating source and the measured temperature of the fluid as the fluid leaves the retractable peristaltic pump.

The processor may control the rotational speed of the pump rotor based upon the measured amount of fluid being pumped by the retractable peristaltic pump.

The processor may control the displacement of the pump rotor based upon the measured pressure of the fluid being pumped by the retractable peristaltic pump.

The processor may control the displacement of the pump rotor based upon the measured temperature of the heating source and the measured temperature of the fluid as the fluid leaves the retractable peristaltic pump.

The processor may control the displacement of the pump rotor based upon the measured amount of fluid being pumped by the retractable peristaltic pump.

The processor may control the rotational direction of the pump rotor to rotate in a first direction when fluid is being pumped into a patient by the retractable peristaltic pump and to rotate in a second direction when waste is being removed from the patient by the retractable peristaltic pump, the first direction is opposite the second direction.

The retractable peristaltic pump assembly may include an encoder, operatively connected to the processor, to measure the rotational speed, the displacement, and the direction of the pump rotor.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. An automated peritoneal dialysis therapy device, comprising:
   a tube set for delivering fluid to a patient and for removing waste from the patient, said tube set including pump tubing;
   a retractable peristaltic pump assembly, operatively connected to said tube set, for causing fluid in said pump tubing to be delivered to the patient and for causing the waste in said pump tubing to be removed from the patient;
   said retractable peristaltic pump assembly including a retractable peristaltic pump;
   said retractable peristaltic pump including a pump base, a pump rotor, and pump rollers; and
   a heating source, located in said pump base of said retractable peristaltic pump, to heat the fluid in said pump tubing, as the fluid is being pumped through said pump tubing, to a predetermined temperature;

said retractable peristaltic pump including a tube locating groove, located in said pump base of said retractable peristaltic pump, to receive said pump tubing;

said heating source being located along a path of said pump tubing received by said tube locating groove of said retractable peristaltic pump;

said heating source being located adjacent to said tube locating groove to transfer heat to the fluid in the pump tubing along said path of said pump tubing received by said tube locating groove of said retractable peristaltic pump.

2. The automated peritoneal dialysis therapy device, as claimed in claim 1, wherein said heating source is an inductive heater coil.

3. The automated peritoneal dialysis therapy device, as claimed in claim 2, wherein said heating source includes an inductive power pulse generator to provide power to said inductive heater coil.

4. The automated peritoneal dialysis therapy device, as claimed in claim 1, wherein said heating source is a resistive heater coil.

5. The automated peritoneal dialysis therapy device, as claimed in claim 1, wherein said tube set is disposable.

6. The automated peritoneal dialysis therapy device, as claimed in claim 1, wherein said tube set includes a connector for connecting to a patient, a Y connector, a first line connected to said Y connector and a second line connected to said Y connector, said first line having a connector for connecting to a fluid source, said second line having a connector for connecting to a waste removal system.

7. The automated peritoneal dialysis therapy device, as claimed in claim 6, wherein said first line includes a one-way fluid valve and said second line includes a one-way fluid valve.

8. The automated peritoneal dialysis therapy device, as claimed in claim 1, further comprising:
   a non-contact flow sensor for measuring a flow and a temperature sensor for measuring a temperature of the fluid.

9. The automated peritoneal dialysis therapy device, as claimed in claim 1, wherein said heating source is integral to said pump base of said retractable peristaltic pump.

10. An automated peritoneal dialysis therapy device comprising:
   a tube set for delivering fluid to a patient and for removing waste from the patient, said tube set including pump tubing;
   a retractable peristaltic pump assembly, operatively connected to said tube set, for causing fluid in said pump tubing to be delivered to the patient and for causing the waste in said pump tubing to be removed from the patient;
   a heating source to heat the fluid in said pump tubing, as the fluid is being pumped through said pump tubing, to a predetermined temperature; and
   a processor for controlling operations of the automated peritoneal dialysis therapy device;
   said retractable peristaltic pump assembly including,
      a retractable peristaltic pump, said retractable peristaltic pump including a pump base, a pump rotor, and pump rollers,
      a heating source temperature sensor to measure a temperature of said heating source,
      a fluid temperature sensor to measure a temperature of the fluid in said pump tubing as the fluid in said pump tubing leaves said retractable peristaltic pump,
      a flow sensor to measure an amount of fluid in said pump tubing being pumped by said retractable peristaltic pump,
      a pressure sensor to measure a pressure of the fluid in said pump tubing being pumped by said retractable peristaltic pump, and
      a motor assembly to rotate said pump rotor to pump the fluid in said pump tubing to the patient and to rotate said pump rotor to draw waste from said patient and pump the waste to a waste removal system;
   said retractable peristaltic pump including a tube locating groove, located in said pump base of said retractable peristaltic pump, to receive said pump tubing;
   said heating source being located in said pump base of said retractable peristaltic pump;
   said heating source being located along a path of said pump tubing received by said tube locating groove of said retractable peristaltic pump;
   said heating source being located adjacent to said tube locating groove to transfer heat to the fluid in the pump tubing along said path of said pump tubing received by said tube locating groove of said retractable peristaltic pump;
   said processor being operatively connected to said heating source temperature sensor, said fluid temperature sensor, said flow sensor, said pressure sensor, said heating source, and said motor assembly;
   said processor controlling a rotational speed, a displacement, and a direction of said pump rotor.

11. The automated peritoneal dialysis therapy device, as claimed in claim 10, wherein said processor controls the rotational speed of said pump rotor based upon the measured pressure of the fluid in said pump tubing being pumped by said retractable peristaltic pump.

12. The automated peritoneal dialysis therapy device, as claimed in claim 10, wherein said processor controls the rotational speed of said pump rotor based upon the measured temperature of said heating source and the measured temperature of the fluid in said pump tubing as the fluid leaves said retractable peristaltic pump.

13. The automated peritoneal dialysis therapy device, as claimed in claim 10, wherein said processor controls the rotational speed of said pump rotor based upon the measured amount of fluid in said pump tubing being pumped by said retractable peristaltic pump.

14. The automated peritoneal dialysis therapy device, as claimed in claim 10, wherein said processor controls the displacement of said pump rotor based upon the measured pressure of the fluid in said pump tubing being pumped by said retractable peristaltic pump.

15. The automated peritoneal dialysis therapy device, as claimed in claim 10, wherein said processor controls the displacement of said pump rotor based upon the measured temperature of said heating source and the measured temperature of the fluid in said pump tubing as the fluid leaves said retractable peristaltic pump.

16. The automated peritoneal dialysis therapy device, as claimed in claim 10, wherein said processor controls the displacement of said pump rotor based upon the measured amount of fluid in said pump tubing being pumped by said retractable peristaltic pump.

17. The automated peritoneal dialysis therapy device, as claimed in claim 10, wherein said processor controls the rotational direction of the pump rotor to rotate in a first direction when fluid in said pump tubing is being pumped into a patient by said retractable peristaltic pump and to rotate in a second direction when waste is being removed from the patient by said retractable peristaltic pump, said first direction is opposite said second direction.

18. The automated peritoneal dialysis therapy device, as claimed in claim 10, wherein said retractable peristaltic pump assembly includes an encoder, operatively connected to said processor, to measure the rotational speed, the displacement, and the direction of said pump rotor.

19. An automated peritoneal dialysis therapy device, comprising:
- a retractable peristaltic pump assembly for causing fluid in a pump tubing to be delivered to the patient and for causing the waste in the pump tubing to be removed from the patient;
- said retractable peristaltic pump assembly including a retractable peristaltic pump;
- said retractable peristaltic pump including a pump base, a pump rotor, and pump rollers; and
- a heating source, located in said pump base of said retractable peristaltic pump, to heat the fluid in the pump tubing, as the fluid is being pumped through the pump tubing, to a predetermined temperature;
- said retractable peristaltic pump including a tube locating groove, located in said pump base of said retractable peristaltic pump, to receive the pump tubing;
- said heating source being located along a path of the pump tubing received by said tube locating groove of said retractable peristaltic pump;
- said heating source being located adjacent to said tube locating groove to transfer heat to the fluid in the pump tubing along the path of the pump tubing received by said tube locating groove of said retractable peristaltic pump.

* * * * *